United States Patent [19]

Lies et al.

[11] 4,011,230

[45] Mar. 8, 1977

[54] DITHIOCARBAMATE ESTER BACTERICIDES AND FUNGICIDES

[75] Inventors: Thomas Andrew Lies, Montgomery Township; James Wellington Clapp, Princeton, both of N.J.

[73] Assignee: American Cyanamid Company, Stamford, Conn.

[22] Filed: Apr. 14, 1975

[21] Appl. No.: 567,664

Related U.S. Application Data

[62] Division of Ser. No. 323,169, Jan. 12, 1973, abandoned, which is a division of Ser. No. 127,825, March 24, 1971, Pat. No. 3,723,494.

[52] U.S. Cl. .................. 260/293.85; 260/293.64; 260/293.71; 260/293.73; 260/326.83; 260/329 S; 260/455 A; 260/347.2; 424/267; 424/274; 424/300; 260/293.63; 260/306.7 R

[51] Int. Cl.² ............. C07D 401/12; C07D 403/12

[58] Field of Search ................ 260/293.63, 293.64, 260/293.71, 293.73, 293.85, 326.83, 455 A, 329 S, 347.2

[56] References Cited

UNITED STATES PATENTS

| | | | |
|---|---|---|---|
| 2,384,577 | 9/1945 | Thomas | 260/293.63 |
| 2,524,081 | 10/1950 | Ritter | 260/293.63 |
| 3,248,400 | 4/1966 | Flieg | 260/293.63 |
| 3,579,516 | 5/1971 | Albert et al. | 260/293.63 |
| 3,723,494 | 3/1973 | Lies et al. | 260/455 A |

*Primary Examiner*—Henry R. Jiles
*Assistant Examiner*—Robert T. Bond
*Attorney, Agent, or Firm*—H. G. Jackson

[57] ABSTRACT

The present invention relates to certain novel dithiocarbamate esters, methods for their synthesis and their use as bactericidal and fungicidal agents.

7 Claims, No Drawings

DITHIOCARBAMATE ESTER BACTERICIDES AND FUNGICIDES

This is a division of application Ser. No. 323,169, filed Jan. 12, 1973, now abandoned which is a division of application Ser. No. 127,825 filed Mar. 24, 1971, now U.S. Pat. No. 3,723,494.

In one respect, the present invention relates to novel dithiocarbamate esters having structures selected from the group consisting of:

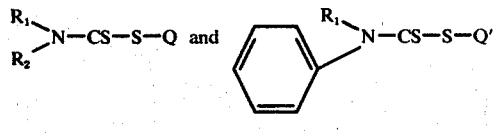

I    II where Q is a member selected from the group consisting of:

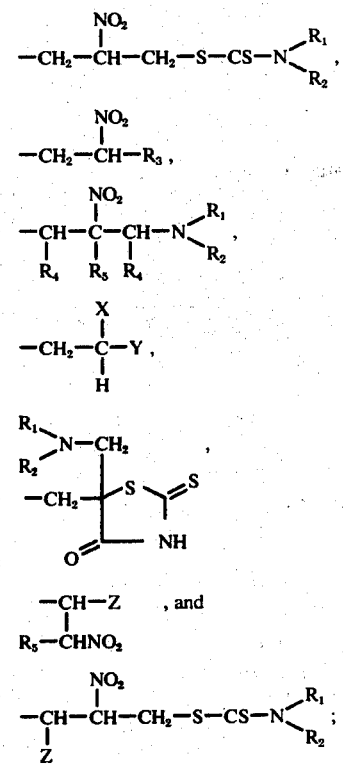

Q' is a member selected from the group consisting of:

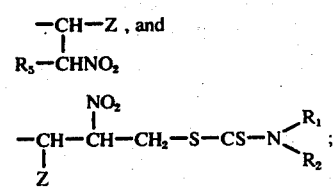

$R_1$ and $R_2$ are loweralkyl of from $C_1$–$C_4$, or when $R_1$ and $R_2$ are taken together with N form a piperidine or pyrrolidine nucleus;
$R_3$ is a loweralkyl of from $C_1$–$C_3$;
$R_4$ is hydrogen, phenyl or substituted phenyl;
$R_5$ is hydrogen or loweralkyl of from $C_1$–$C_4$;
X is acetyl or benzoyl;
Y is acetyl or

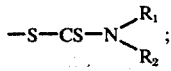

and Z is phenyl,

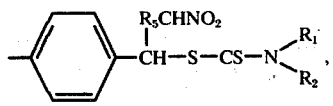

1-naphthyl, 2-furyl, 2-thienyl, 5-chloro-2-thienyl, and substituted phenyl including 3,4-methylenedioxyphenyl, 4-methoxy, 4-bromo, 3,4-dichloro, 2-chloro, 4-isopropyl, 2-acetoxy-3-methoxy, 3,4-dimethoxy, 4-acetoxy and 2-chloro-5-nitrophenyl.

The present invention also relates to the use of the above-identified dithiocarbamate esters as antibacterial and antifungal agents effective for protecting living plants from attack by such pathogenic organisms. The invention further relates to processes for the processes for the preparation of these new dithiocarbamate esters.

In accordance with the invention, Type (1) compounds having the structure:

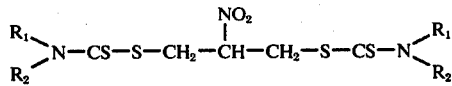

can be prepared by reacting an appropriately substituted dialkylammonium dialkyldithiocarbamate with formaldehyde in the presence of nitromethane. However, when benzaldehyde is employed in this reaction, the α-(nitromethyl)benzyl dimethyldithiocarbamate is formed and treatment of this product with additional dialkylammonium dialkyldithiocarbamate in the presence of formaldehyde yields the phenyl-substituted compound (i.e., Type (7) where Z is phenyl). Similarly, treatment of any of the Type (6) compounds in which $R_5$ is hydrogen with additional dialkylammonium dialkyldithiocarbamate and formaldehyde in the presence of carbon disulfide yields the Type (7) dialkyldithiocarbamate esters. The reactions are preferably run in the presence of carbon disulfide and at a reaction temperature not exceeding about 50° C. Generally, about two moles equivalents of the dialkyldithiocarbamate and two mole equivalents of the aldehyde per mole equivalent of the nitromethane are used.

Graphically, these reactions may be illustrated as follows:

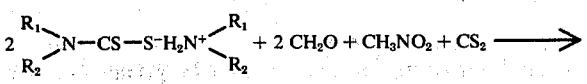

(a)

-continued

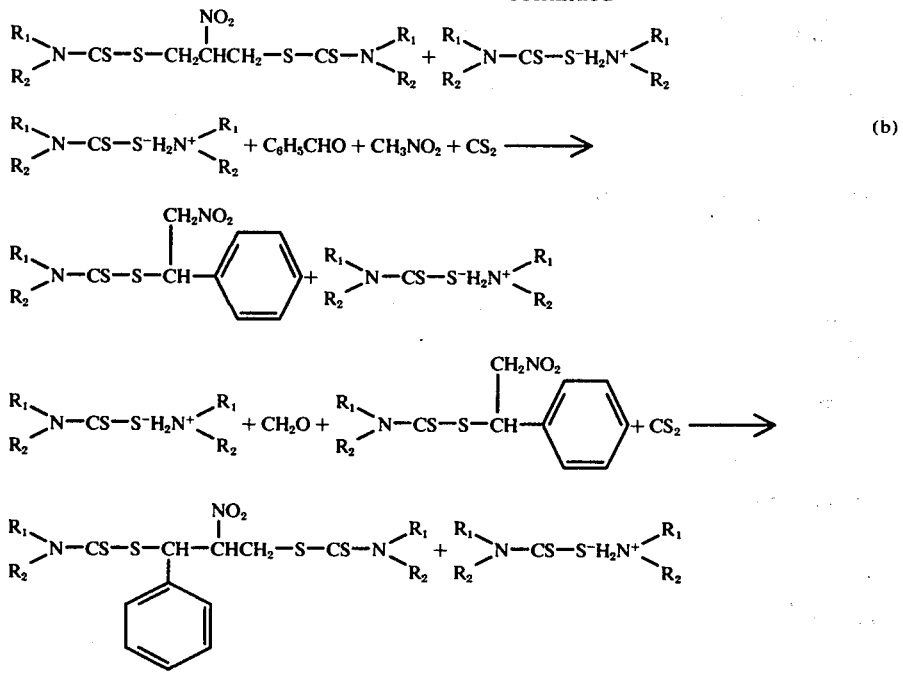
(b)

Compounds of Type (2) having the structure:

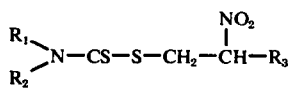

wherein $R_1$, $R_2$ and $R_3$ are as defined above, can be prepared in much the same manner as Type (1) compounds excepting that an appropriately substituted 1-nitroalkane is used in approximately equimolar amounts with respect to the formaldehyde and the dialklyammonium dialkyldithiocarbamate. The reaction is preferably carried out in a lower alcohol such as methanol, ethanol, isopropyl alcohol or butanol containing carbon disulfide at a temperature maintained below about 50° C. These reactions are graphically illustrated below:

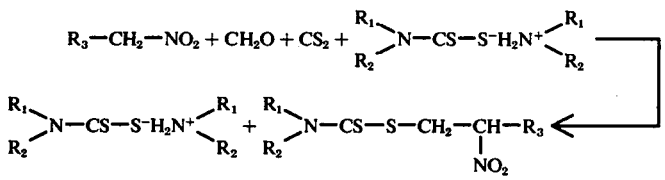

Type (3) compounds are readily prepared by reacting approximately one mole equivalent of nitroalkane with one mole equivalent of an appropriately substituted dialkylammonium dialkyldithiocarbamate, preferably dissolved in a lower alcohol of from $C_1$–$C_4$, and two mole equivalents of an appropriate aldehyde. The reaction is preferably carried out at a temperature below about 50° C. and is graphically illustrated as follows:

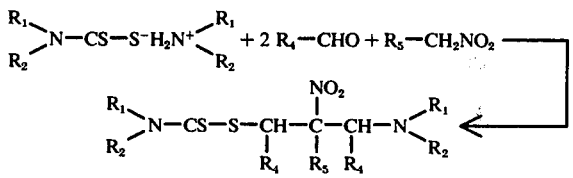

In the above reaction $R_1$, $R_2$, $R_4$, and $R_5$ have the meanings set forth above. Where $R_4$ is substituted phenyl, there may be one or two substituents included on the ring, and the substituents may be any of the group selected from the halogens (i.e., chloro, fluoro, bromo, or iodo), methyl or ethyl, m-nitro, methoxy or ethoxy.

Compounds of Type (4) can be prepared by reacting essentially equimolar amounts of a dialkylammonium dialkyldithio-carbamate with formaldehyde and (1) a phenacyl or acetonyl dialkyldithiocarbamate or (2) 2,4-pentanedione in the presence of carbon disulfide and at a temperature below about 50° C. The reaction may be graphically written:

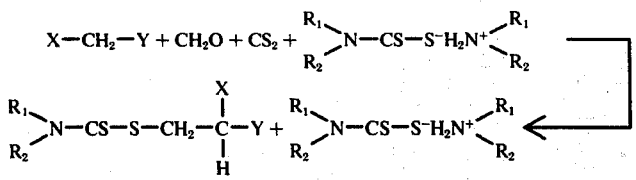

and $R_1$, $R_2$, X and Y are as defined above.

Compounds of Type (5) are synthesized by reacting a dialkylammonium dialkyldithiocarbamate with approximately an equimolar amount of rhodanine and formaldehyde with about one-half molar amount of carbon disulfide in a lower alcohol $C_1$–$C_4$. The reaction is generally carried out at a temperature below 50° C. The reaction may be illustrated as follows:

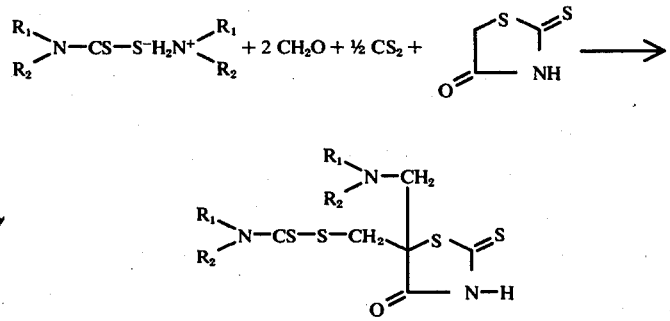

wherein $R_1$ and $R_2$ are as described above.

Type (6) compounds which have the formula structure:

wherein $R_1$, $R_2$, $R_5$ and Z are as previously defined can be prepared by reacting a dialkylammonium dialkyldithiocarbamate with a nitrovinyl compound in a lower alcohol or dimethylformamide solution containing carbon disulfide at from 10° C.–50° C.

Preparation of Type (6) compounds may be illustrated as follows:

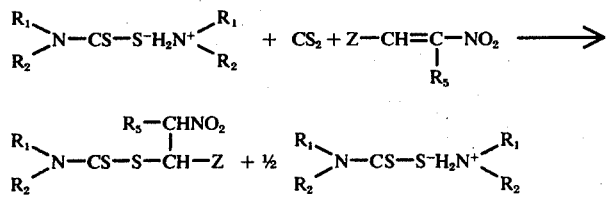

The required dialkylammonium dialkyldithiocarbamate may be prepared in a separate reaction for use in the above reaction, or for greater process economy, it may be formed in the reaction mixture by gradual addition of the amine to a solution of the nitrovinyl compound and carbon disulfide.

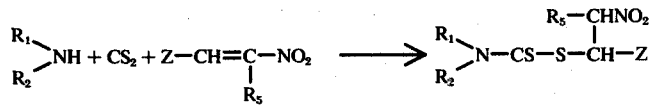

When the ammonium salt of a dialkyldithiocarbamic acid is employed, an acid such as acetic acid or hydrochloric acid is added as required in portions as the reaction proceeds, so that the concentration of free ammonia is minimized. An excess of acid at any time is to be avoided.

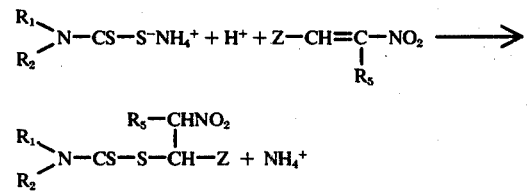

Type (6) compounds having the formula structure:

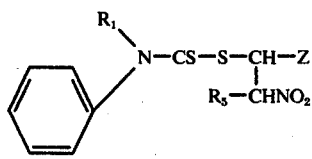

wherein $R_1$, $R_5$ and Z are as previously defined, can be prepared by reacting an ammonium alkyldithiocarbanilate with a nitrovinyl compound in lower alcohol, $C_1$–$C_4$, or dimethylformamide solution at 0° C.–50° C. with the addition of an acid such as acetic or hydrochloric acid as required in portions as the reaction proceeds, so that the concentration of free ammonia in the reaction mixture is minimized:

the reaction medium are isolated by diluting the reaction mixture with water and extracting the products from the mixture with ether, methylene chloride or other suitable water-immiscible solvent. Further purification is accomplished by recrystallization or chromatography.

The generic process equations for structures (1), (2), (4) and (6) show that amines are liberated as a by-pro-

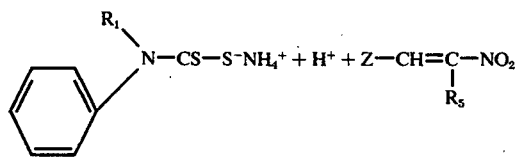 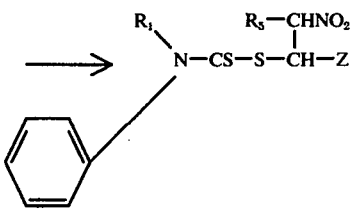

Compounds of Type (7) can be prepared by reacting dithiocarbamate esters having the formula structures:

duct of the reactions. It is considered part of the invention that removal of the liberated amine (as by proton-

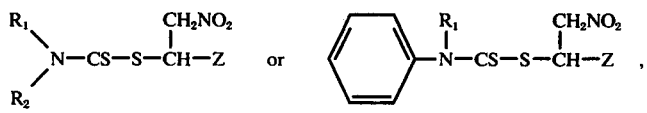

with equimolar amounts of formaldehyde and a dialkylammonium dialkyldithiocarbamate in aqueous lower alcohol, $C_1$–$C_4$, or aqueous dimethylformamide solution containing carbon disulfide at a temperature of from 20° C.–50° C. The reactions may be graphically written:

ation, reaction with carbon disulfide, or other chemical combination) results in higher yields of purer products.

In Example 15, the preparation of α-(nitromethyl)-benzyl 1-pyrrolidinecarbodithioate from ammonium 1-pyrrolidinecarbodithioate, acetic acid was added at the end of the reaction to combine with the liberated

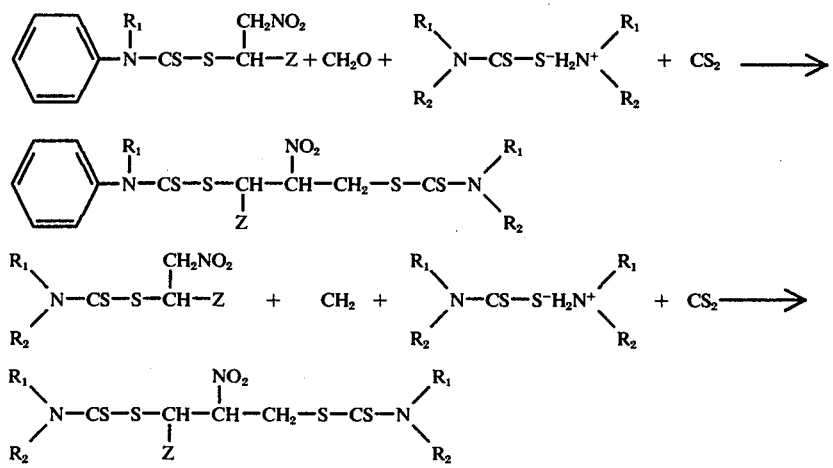

Type (1) compounds are exemplified in Examples 1 through 3, Type (2) in Examples 5 and 6, Type (3) in Examples 7 and 8, Type (4) in Examples 9 through 11, Type (5) in Example 12, Type (6) in Examples 13 through 35, and Type (7) in Example 4.

Although some examples show different molar ratios of reactants, the processes are advantageously carried out with the quantities of reactants shown in the generic process equations.

Suitable solvents for the reactions are anhydrous or aqueous, one or more normal or iso-lower aliphatic alcohols, $C_1$–$C_4$, and dimethylformamide. recrystallization When the product precipitates from the reaction mixture, it is isolated by filtration. Products soluble in ammonia.

In Example 35, the preparation of α-(nitromethyl)-benzyl N-methyldithiocarbanilate, acetic acid was added in portions during the reaction to combine with the liberated ammonia.

In nearly all other examples where an amine is liberated, sufficient carbon disulfide was added to the reaction mixture at the start of the reaction to combine with the amine as it was liberated, to give dithiocarbamate salts as by-products:

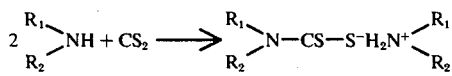

Reduction of the free amine concentration prevents undesirable side reactions, some of which are:

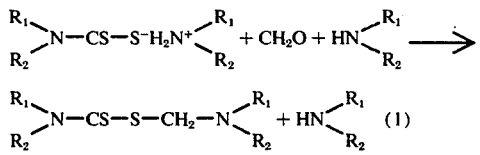

For the β-nitrostyrene reactions:

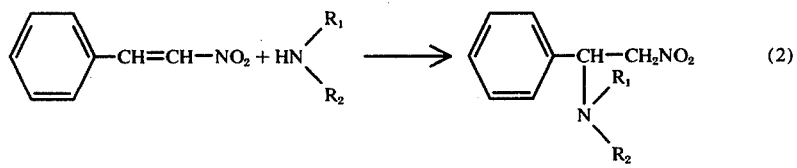

3. Polymerization of the β-nitrostyrene.
4. For all products where a >CH—NO₂ moiety is in the presence of formaldehyde:

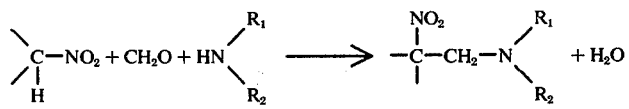

The compounds of the present invention are useful as antibacterial and antifungal agents and are particularly effective for protecting agronomic crops, both growing and harvested, from attack by pathogenic bacteria and fungi.

As used herein, the term "agronomic crops" is meant to include (1) field crops such as grains, forage, paasturage, oil and seed crops, fibers, roots and tubers, sugar and specialities such as tobacco and hops, and (2) horticultural crops such as tree fruits and citrus fruits, berries and grapes, nuts, vegetables, herbs, ornamentals, flowers and the like. These compounds may also be used for the protection of leather goods, textiles, and fibers, in the manufacture of paper or pulp and in process water or the like.

In practice, the active compounds are generally prepared as dusts, dust concentrates, wettable powders or the like.

The dusts can be prepared by grinding about 1% to 15% by weight of the active compound with about 99% to 85% by weight of an inert diluent such as kaolin, attaclay, walnut shell flour, talc, pumice, diatomaceous earth or the like.

Dust concentrates are made in similar fashion excepting that percent by weight of active ingredient is increased to about 16% to 75% of the composition.

Wettable powders are prepared in the same manner as dust concentrates, but usually contain, in addition to the active ingredient and solid diluent, from about 1% to 5% by weight of a wetting agent such as sodium isopropylnaphthalene-sulfonate or the sodium salt of a sulfonated napthalene formaldehyde condensate, and from about 1% to 5% by weight of a dispersing agent such as hydroxyethylcellulose. A typical formulation would be 50% by weight of active ingredient, 2% of the dispersing agent, 5% of the wetting agent and 43% attapulgite.

In using wettable powder, the formulated material is generally dispersed in water and applied as a liquid spray to the crops, textiles, fabrics, paper or the like, which are to be protected from attack by fungi. Usually the sprays applied to crops are used in sufficient quantity to provide about ⅛ pound to about 10 pounds per acre of the active dialkyldithiocarbamate.

The invention is further illustrated by the following examples which are not to be taken as being limitative thereof. In each case, parts and percentages are by weight unless otherwise indicated.

EXAMPLE 1

2-Nitrotrimethylene Dimethyldithiocarbamate and Related Compounds

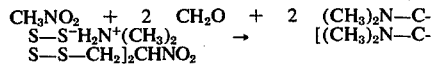

Method A

Nitromethane (9.2 grams, 0.15 mole) was added to a solution of dimethylammonium dimethyldithiocarbamate (18.0 grams, 0.108 mole) and formaldehyde (15.0 grams of 37% aqueous solution, 0.185 mole) in 95% ethanol (50 ml.). The ensuing reaction was first endothermic, and then became exothermic. The reaction temperature was held below 45° with ice-cooling of the vessel. After 1 hour, the reaction mixture was cooled in ice and the precipitated product was filtered off, washed with water, and dried in air. The crude product melted at 130° C.–133° C. and weighed 11.9 grams (67% yield). Three recrystallizations from hot acetone solution gave pure 2-nitrotrimethylene dimethyldithiocarbamate melting at 133° C.–137° C. (prior sintering, gas evolution). The structure was determined by infrared and nuclear magnetic resonance spectra and elemental analysis.

Analysis Calculated for $C_9H_{17}N_3S_4O_2$: C, 33.01; H, 5.23; N, 12.83; S, 39.16. Found: C, 33.24; H, 5.24; N, 12.86; S, 39.15.

Method B

In the improved process, nitromethane (153 grams, 2.5 moles) was added dropwise to a stirred solution of formaldehyde (410 grams of 37% aqueous solution, 5.0 moles), dimethylammonium dimethyldithiocarbamate (800 grams, 4.8 moles), and carbon disulfide (152 ml., 2.5 moles) in methanol (1500 ml.). Rate of addition was adjusted to maintain a reaction temperature of about 30° C. After 4 hours from the start of the reaction, the reaction mixture was cooled to 5° C. and the precipitated product was filtered off, washed with cold methanol and water, and dried in air. The yield of 2-nitrotrimethylene dimethyldithiocarbamate melting at 130° C.–135° C. (prior sintering, gas evolution) was 750 grams (91%).

Following either Method A or B but substituting diisopropylammonium diisopropyldithiocarbamate, ethylmethylammonium ethylmethyldithiocarbamate, or dibutylammonium dibutyldithiocarbamate for dimethylammonium dimethyldithiocarbamate yields the corresponding 2-nitrotrimethylene diisopropyldithiocarbamate, 2-nitrotrimethylene ethylmethyldithiocarbamate, or 2-nitrotrimethylene dibutyldithiocarbamate.

Following either Method A or B but substituting 95% ethanol or 2-propanol for methanol yields 2-nitrotrimethylene dimethyldithiocarbamate.

EXAMPLE 2

2-Nitrotrimethylene Diethyldithiocarbamate $$2\ (C_2H_5)_2N-CS-S^-H_2N^+(C_2H_5)_2 + 2\ CH_2O + CS_2 + CH_3NO_2 \rightarrow [(C_2H_5)_2N\text{-}CS\text{-}S\text{-}CH_2]_2CHNO_2$$

Formaldehyde (16.4 grams of 37% aqueous solution, 0.2 mole) and nitromethane (9.2 grams, 0.15 mole) were added to a solution of diethylammonium diethyldithiocarbamate (22.2 grams, 0.1 mole) and carbon disulfide (7.6 grams, 0.10 mole) in ethanol (175 ml.). The temperature of the resulting reaction was kept below 35° C. with a cooling bath. After 1 hour the product was filtered off, washed with ethanol and ether, and dried in air. The crude product, which weighed 22.9 grams, was recrystallized from 2-propanol to give 2-nitrotrimethylene diethyldithiocarbamate melting at 90° C.–91° C. The structure was determined from infrared and nuclear magnetic resonance spectra and elemental analysis.

Analysis Calculated for $C_{13}H_{25}N_3S_4O_2$: C, 41.11; H, 6.55; N, 10.95; S, 33.43. Found: C, 41.15; H, 7.04; N, 11.28; S, 33.68.

2-Nitrotrimethylene diethyldithiocarbamate was also obtained from the above reactants in dimethylformamide solution.

EXAMPLE 3

2-Nitrotrimethylene 1-Piperidinecarbodithioate

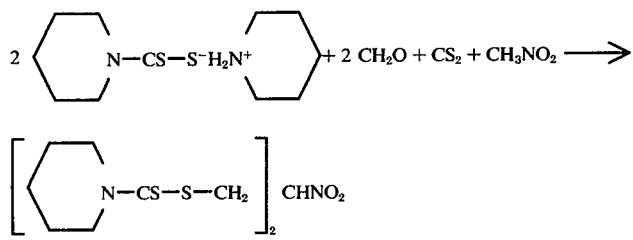

Piperidinium 1-piperidinecarbodithioate (49.2 grams, 0.20 mole), formaldehyde (16.2 grams of 37% aqueous solution, 0.20 mole), carbon disulfide (7.6 grams, 0.10 mole) and nitromethane (6.1 grams, 0.10 mole) were dissolved in methanol (200 ml.). A mildly exothermic reaction resulted, and after 2.5 hours, the reaction mixture was cooled to 1° C. and the product was filtered off, washed with water, and dried in air. The crude product melted at 108.5° C.–120° C. Repeated recrystallization from unheated methylene chloride-hexane solution gave 2-nitrotrimethylene 1-piperidinecarbodithioate melting at 128.5° C.–133° C. (prior sintering, gas evolution). The structure of the product was determined from infrared and nuclear magnetic resonance spectra and elemental analysis.

Analysis Calculated for $C_{15}H_{25}N_3S_4O_2$: C, 44.20; H, 6.18; N, 10.31; S, 31.46. Found: C, 44.31; H, 6.22; N, 10.24; S, 31.74.

EXAMPLE 4

2-Nitro-1-phenyltrimethylene Dimethyldithiocarbamate and Related

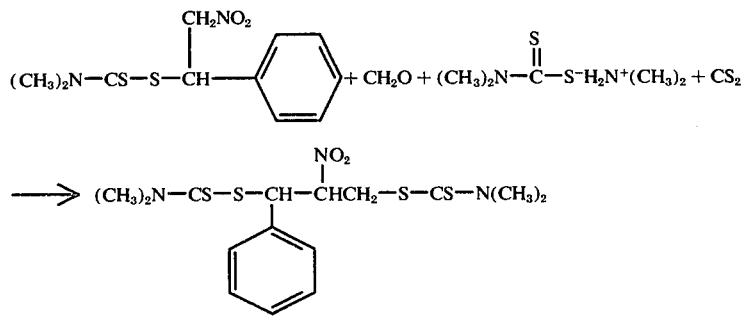

A mixture of α-(nitromethyl)benzyl dimethyldithiocarbamate (8.1 grams, 0.030 mole), formaldehyde (2.4 grams of 37% aqueous solution, 0.030 mole), dimethylammonium dimethyldithiocarbamate (5.0 grams, 0.030 mole), and carbon disulfide (2.3 grams 0.030 mole) in 15 ml. of dimethylformamide was allowed to stand at 25° C. No exotherm was apparent, but within 3 hours a solid began to precipitate. After 22 hours, the reaction mixture, a moist cake, was diluted with acetone (100 ml.) and the solid was filtered off. The white crude product, m.p. 142° C.–146.5° C. (gas evolution), weighed 10 grams (83% yield). Repeated recrystallization from methylene chloride-hexane solution without heat gave pure 2-nitro-1-phenyltrimethylene dimethyldithiocarbamate, melting at 145° C.–151° C. (sinter 143° C., gas evolution.

Analysis Calculated for $C_{15}H_{21}N_3S_4O_2$: C, 44.64; H, 5.25; N, 10.41; S, 31.78. Found: C, 44.99; H, 5.30; N, 10.45; S, 32.14.

Reaction of 3,4-dimethoxy-α-(nitromethyl)benzyl ethyldithiocarbanilate with formaldehyde and dimethylammonium dimethyldithiocarbamate in the presence of carbon disulfide yields 3,4-dimethoxy-α-(2-mercapto-1-nitroethyl)benzyl ethyldithiocarbanilate ester with dimethyldithiocarbamic acid.

Employing the above procedure but substituting α-(nitromethyl)benzyl ethylmethyldithiocarbamate for α-(nitro-methyl)benzyl dimethyldithiocarbamate yields α-(2-mercapto-1-nitroethyl)benzyl ethylmethyldithiocarbamate ester with dimethyl-dithiocarbamic acid.

Also using α-(nitromethylene)benzyl ethylmethyldithiocarbamate and ethylmethylammonium ethylmethyldithiocarbamate in the above reaction yields 2-nitro-1-phenyltrimethylene ethylmethyldithiocarbamate.

Also, using p-bromo-α-(nitromethyl)benzyl dimethyldithiocarbamate and dimethylammonium dimethyldithiocarbamate yields 2-nitro-1-(p-bromophenyl)-trimethylene dimethyldithiocarbamate.

EXAMPLE 5

2-Nitropropyl Dimethyldithiocarbamate and Related Compounds

Nitroethane (7.5 grams, 0.10 mole) was added in one portion to a solution of formaldehyde (8.1 grams of 37% aqueous solution, 0.10 mole), carbon disulfide (7.6 grams, 0.10 mole), and dimethylammonium dimethyldithiocarbamate (16.6 grams, 0.10 mole) in 95% ethanol (50 ml.) and the resulting solution was kept at 23° C. for 21 hours. The solution was then poured into water (850 ml.) and the precipitated oil was taken up in methylene chloride. The dried solution was concentrated in a rotary evaporator to leave an oil which was chromatographed on Florisil and silica gel to leave 6.5 grams of an amber oil which was crystallized from 30 ml. of cold methanol to give 5.7 grams of the product, melting at 37° C.–42.5° C. Repeated recrystallizations without heat from methanol and ethanol gave pure 2-nitropropyl dimethyldithiocarbamate melting at 38.5° C.–41° C. The structure was proved by infrared and nuclear magnetic resonance spectra and elemental analysis.

Analysis Calculated for $C_6H_{12}N_2S_2O_2$: C, 34.59; H, 5.81; N, 13.45; S, 30.78. Found: C, 34.77; H, 5.92; N, 13.41; S, 30.54.

Substitution of di-n-butylammonium di-n-butyldithiocarbamate for dimethylammonium dimethyldithiocarbamate in the above reaction yields the 2-nitropropyl di-n-butyldithiocarbamate. Similarly, the 2-nitropropyl ethylmethyldithiocarbamate can be prepared using the ethylmethylammonium ethylmethyldithiocarbamate. Moreover, when nitropropane is substituted in any of these reactions, the corresponding 2-nitrobutyl dialkyldithiocarbamate iis formed.

EXAMPLE 6

2-Nitrobutyl Dimethyldithiocarbamate and Related Compounds

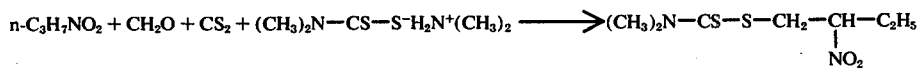

Nitropropane (17.8 grams, 0.20 mole), formaldehyde (16.2 grams of 37% aqueous solution, 0.20 mole), carbon disulfide (15.2 grams, 0.20 mole), and dimethylammonium dimethyldithiocarbamate (33.2 grams, 0.20 mole) were dissolved in methanol (100 ml.). A mildly exothermic reaction resulted. After 21.5 hours, the reaction mixture was poured into water (850 ml.) and the precipitated oil was washed with water and then taken up in methylene chloride. The dried solution was concentrated in a rotary evaporator to leave an amber oil. A small sample of the product was chromatographed on Florisil adsorbant giving an oil which solidified when chilled in methanol solution. The main sample crystallized from cold methanol solution when it was seeded. Repeated recrystallization from cold methanol gave pure 2-nitrobutyl dimethyldithiocarbamate melting at about 23° C. The structure was determined from infrared and nuclear magnetic resonance spectra and elemental analysis.

Analysis Calculated for $C_7H_{14}N_2O_2S_2$: C, 37.82; H, 6.35; N, 12.60; S, 28.84. Found: C, 37.99; H, 6.43; N, 12.66; S, 28.60.

Substituting diisopropylammonium diisopropyldithiocarbamate for dimethylammonium dimethyldithiocarbamate in the above reaction yields 2-nitrobutyl diisopropyldithiocarbamate.

EXAMPLE 7

3-Dimethylamino-2-methyl-2-nitropropyl Dimethyldithiocarbamate

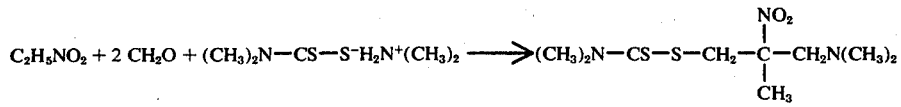

Nitroethane (7.5 grams, 0.10 mole) was added to a solution of formaldehyde (18 grams of 37% aqueous solution) and dimethylammonium dimethyldithiocarbamate (33.2 grams, 0.20 mole) in 95% ethanol (80 ml.). The resulting solution was warmed briefly to 32° C., and was then allowed to stand. After 20 hours, the reaction mixture was cooled in ice and the product was filtered off. The yield of crude product melting at 65.5° C.-68.2° C. was 22 grams (83%). Recrystallizations without heat from carbon tetrachloride-hexane solution gave pure 3-dimethylamino-2-methyl-2-nitropropyl dimethyldithiocarbamate melting at 75.5° C.-78° C. The structure was determined by infrared and nuclear magnetic resonance spectra and elemental analysis.

Analysis Calculated for $C_9H_{19}N_3S_2O_2$: C, 40.73; H, 7.22; N, 15.83; S, 24.16. Found: C, 40.72; H, 7.14; N, 15.76; S, 24.39.

EXAMPLE 8

1,3-Bis(2,4-dichlorophenyl)-3-dimethylamino-2-nitropropyl Dimethyldithiocarbamate and Related Compounds

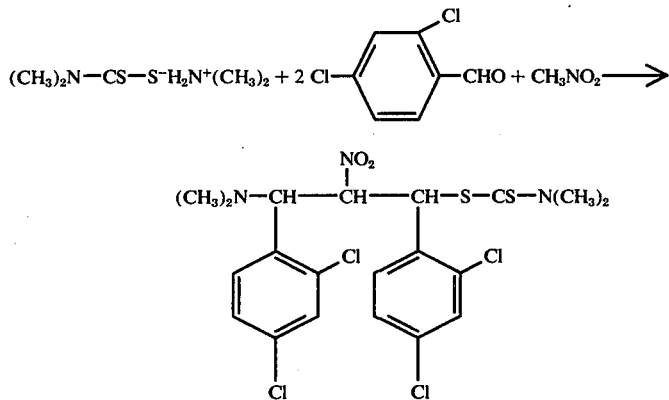

A solution of dimethylammonium dimethyldithiocarbamate (16.6 grams, 0.10 mole), 2,4-dichlorobenzaldehyde (17.4 grams, 0.10 mole) and nitromethane (3.2 grams, 0.050 mole) in 95% ethanol (50 ml.) was allowed to stand at 23° C. for 24 hours. The resulting precipitate was filtered off, washed with cold 95% ethanol, and dried in air. Recrystallization from acetone-ethanol solution (without heating) gave 1,3-bis(2,4-dichlorophenyl)- 3-dimethylamino-2-nitropropyl dimethyldithiocarbamate melting at 152° C.-154° C.

The structure of the product was determined from infrared and nuclear magnetic resonance spectra and elemental analysis.

Analysis Calculated for $C_{20}H_{21}N_3O_2S_2Cl_4$: C, 44.37; H, 3.91; N, 7.76; S, 11.86; Cl, 26.19. Found: C, 44.43; H, 3.78; N, 7.72; S, 11.78; Cl, 26.40.

Substituting benzaldehyde for 2,4-dichlorobenzaldehyde in the above reaction yields 1,3-diphenyl-3-dimethylamino-2-nitropropyl dimethyldithiocarbamate. Also substituting ethylmethylammonium ethylmethyldithiocarbamate for dimethylammonium dimethyldithiocarbamate in the above reaction yields 1,3-bis-(2,4-dichlorophenyl)-3-ethylmethylamino-2-nitrophenyl ethylmethyldithiocarbamate.

EXAMPLE 9

2-(1-Hydroxyethylidene)-3-oxobutyl Dimethyldithiocarbamate and Related Compounds

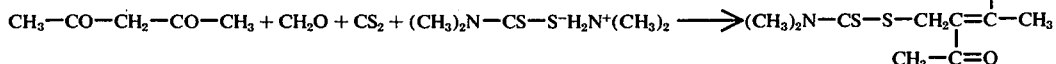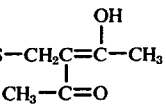

Dimethylammonium dimethyldithiocarbamate (33.2 grams, 0.20 mole), formaldehyde (16.2 grams of 37% aqueous solution, 0.20 mole), 2,4-pentanedione (20.0 grams, 0.20 mole), and carbon disulfide (15.2 grams, 0.20 mole) were dissolved in methanol (100 ml.). The temperature of the resulting reaction was kept below 27° C. with ice cooling. After 3 hours at 22° C.-29° C., the reaction mixture was cooled in ice and the precipitated product was filtered off, washed with cold methanol and water, and dried in air. The crude product, melting at 69.5° C.-71.5° C. (prior sintering) weighed 37.3 grams (80%). Repeated precipitation of the material from carbon tetrachloride solution by the addition of hexane gave pure 2-(1-hydroxyethylidene)-3-oxobutyl dimethyldithiocarbamate melting at 70° C. -72° C. The structure was determined from infrared and nuclear magnetic resonance spectra and elemental analysis.

Analysis Calculated for $C_9H_{15}NS_2O_2$: C, 46.32; H, 6.48; N, 6.00; S, 27.48. Found: C, 46.54; H, 6.43; N, 5.98; S, 27.08.

2.-(1-Hydroxyethylidene)-3-oxobutyl ethylmethyldithiocarbamate is prepared by substituting ethylmethylammonium ethylmethyldithiocarbamate for dimethylammonium dimethyldithiocarbamate in the above reaction.

EXAMPLE 10

Acetylethylene Dimethyldithiocarbamate and Related Compounds

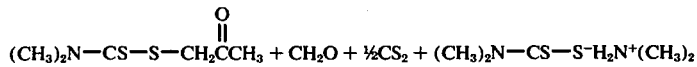

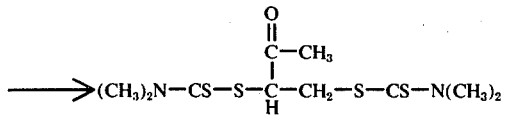

A solution of acetonyl dimethyldithiocarbamate (3.6 grams, 0.020 mole), formaldehyde (1.6 grams of 37% aqueous solution, 0.020 mole), carbon disulfide (0.010 mole, 0.8 gram), and dimethylammonium dimethyldithiocarbamate (3.3 grams, 0.02 mole) in methanol (15 ml.) was stirred and heated at 39° C.–43° C. for 160 minutes. The reaction mixture was then cooled in ice and the precipitated product was filtered off, washed with cold methanol, and dried in air. The yield of product melting at 104° C.–106.5° C. (prior sintering) was 5.2 grams (84%). Repeated recrystallization from methylene chloride-methanol solution without heat gave the analytical sample of 1-acetylethylene dimethyldithiocarbamate melting at 105° C.–107.5° C. (prior sintering). The structure was determined from the infrared spectrum and elemental analysis.

Analysis Calculated for $C_{10}H_{18}N_2S_4O$: C, 38.68; H, 5.84; N, 9.02; S, 41.30. Found: C, 38.92; H, 5.85; N, 9.19 S, 42.30.

Acetylethylene diisopropyldithiocarbamate, acetylethylene di-n-butyldithiocarbamate and acetylethylene ethylpropyldithiocarbamate can all be made by the above procedure by substituting the corresponding acetonyl dialkyldithiocarbamate and dialkylammonium dialkyldithiocarbamate for acetonyl dimethyldithiocarbamate and dimethylammonium dimethyldithiocarbamate in the above reaction.

EXAMPLE 11

Benzoylethylene Dimethyldithiocarbamate

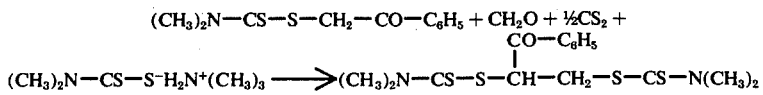

A solution of phenacyl dimethyldithiocarbamate (12.0 grams, 0.050 mole), formaldehyde (4.1 grams of 37% aqueous solution, 0.050 mole), carbon disulfide (1.9 grams, 0.025 mole), and dimethylammonium dimethyldithiocarbamate (8.3 grams, 0.050 mole) in methanol (50 ml.) was stirred and heated at 38° C.–40° C. for 2.5 hours. The reaction mixture was then cooled to 0° C. and the precipitated product was filtered off, washed with cold methanol and dried in air. The yield of product melting at 106° C.–108.5° C. was 17.6 grams (94%). Repeated recrystallization from methylene chloride-methanol and acetone-2-propanol solution without heat gave pure 1-benzoylethylene dimethyldithiocarbamate melting at 106° C.–109.5° C. The structure was determined from the infrared spectrum and elemental analysis.

Analysis Calculated for $C_{15}H_{20}N_2S_4O$: C, 48.35; H, 5.41; N, 7.52; S, 34.42. Found: C, 48.30; H, 5.37; N, 7.49; S, 34.65.

EXAMPLE 12

Dimethyldithiocarbamic Acid S-Ester with 5-(Dimethylaminomethy)-5-(mercaptomethyl)rhodanine

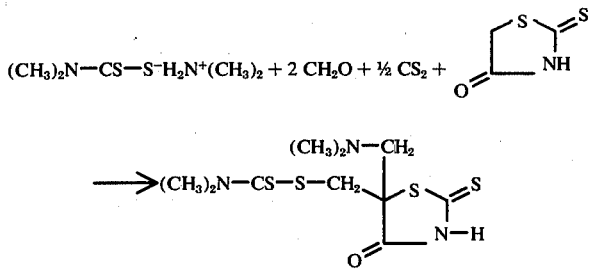

Rhodanine (13.3 grams, 0.10 mole) was added to a solution of dimethylammonium dimethyldithiocarbamate (16.6 grams, 0.10 mole), formaldehyde (8.1 grams of 37% aqueous solution, 0.10 mole), and carbondisulfide (3.8 grams, 0.050 mole) in methanol (50 ml.). The temperature of the resulting exothermic reaction was held to 31° C. with ice cooling. After the exothermic reaction was completed, the reaction mixture was stirred for 2.5 hours at 25° C., and then the yellow product was filtered off, washed with methanol and dried in air. For further purification, the compound was slurried in carbon disulfide and in methanol to give the desired product, melting at 143° C.–145.5° C. (gas evolution). The structure was determined from the infrared spectrum and elemental analysis.

Analysis Calculated for $C_{10}H_{17}N_3S_4O$: C, 37.12; H, 5.30; N, 12.99; S, 39.64. Found: C, 36.98; H, 5.22; N, 12.87; S, 39.84.

EXAMPLE 13
α-(Nitromethyl)benzyl Dimethyldithiocarbamate

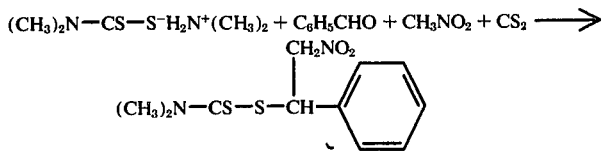

A solution of dimethylammonium dimethyldithiocarbamate (16.6 grams, 0.10 mole), carbon disulfide (7.6 grams, 0.10 mole), benzaldehyde (21.2 grams, 0.20 mole), and nitromethane (9.2 grams, 0.15 mole) in 95% ethanol (50 ml.) was allowed to stand at 23° C. for several days. The resulting precipitate was filtered off, washed with cold 95% ethanol, and dried in air. The solid product, which melted at 101° C.–102° C., was recrystallized from 2-propanol to give α-(nitromethyl)-benzyl dimethyldithiocarbamate melting at 105° C.–106° C. The structure was determined from infrared and nuclear magnetic resonance spectra and elemental analysis.

Analysis Calculated for $C_{11}H_{14}N_2S_2O_2$: C, 48.86; H, 5.21; N, 10.36; S, 23.71. Found: C, 49.31; H, 5.07; N, 10.51; S, 23.92.

EXAMPLE 14
2-(Nitromethyl)benzyl Dimethyldithiocarbamate from β-Nitrostyrene

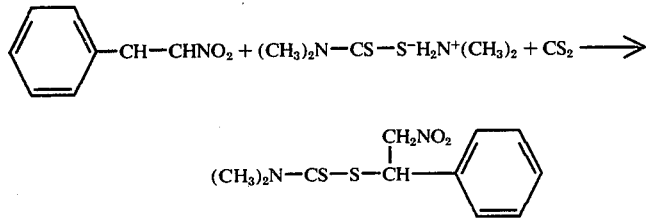

Dimethylammonium dimethyldithiocarbamate (16.6 grams, 0.10 mole), carbon disulfide (7.6 grams, 0.10 mole), and β-nitrostyrene (14.9 grams, 0.10 mole) were dissolved in methanol (50 ml.). A rapid exothermic reaction ensued and the product precipitated. The reaction temperature was held to 35° C. with ice cooling. After several hours at 25° C., the product was filtered off, washed with methanol, and dried in air. The crude product melted at ca. 103° C.–110° C. and weighed 22.9 grams (85%). Recrystallizations from hot methanol and from acetone-2-propanol solution (without heating) gave 13.8 grams of α-(nitromethyl)-benzyl dimethyldithiocarbamate melting at 104° C.–108.5° C. (prior sintering). The infrared spectrum was essentially identical to the spectrum of analytically pure material. When the reaction was repeated with the same proportions except that the carbon disulfide was omitted, the precipitate consisted of about 20% of α-(nitromethyl)benzyl dimethyldithiocarbamate and about 80% of a resinous by-product.

EXAMPLE 15
α-(Nitromethyl)benzyl 1-Pyrrolidinecarbodithioate

β-Nitrostyrene (7.5 grams, 0.050 mole) was added to a cooled (10° C.) stirred slurry of ammonium 1-pyrrolidinecarbodithioate (8.2 grams, 0.050 mole) in methanol (50 ml.). The temperature of the mixture fell to 5° C., then rapidly climbed to 10° C. The cooling bath was removed and the reaction temperature rose slowly to 22° C. Acetic acid (3.0 grams, 0.05 mole) was added, the slurry was cooled to 10° C. and the solid was filtered off, washed with water, and dried in air. The crude product melted at 108° C.–116° C. and weighed 11.4 grams (77% yield). Repeated recrystallizations from cool acetone-methanol, hot acetone-2-propanol, and cool methylene chloride-toluene-hexane solutions gave pure α-(nitromethyl)benzyl 1-pyrrolidinecarbodithioate melting at 116° C.–120° C. (sintering at 113° C.).

Analysis Calculated for $C_{13}H_{16}N_2S_2O_2$: C, 52.68; H, 5.44; N, 9.45; S, 21.63. Found: C, 53.01; H, 5.28; N, 9.47; S, 22.02.

EXAMPLE 16
α-(Nitromethyl)benzyl 1-Piperidinecarbodithioate

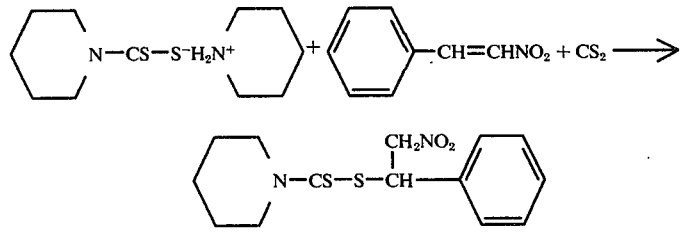

β-Nitrostyrene (14.9 grams, 0.10 mole) was added in portions to a stirred mixture of piperidinium 1-piperidinecarbodithioate (24.6 grams, 0.10 mole), and carbon disulfide (7.6 grams, 0.10 mole) in methanol (200 ml.). During the addition, the reaction temperature was 25° C.–29° C. After the addition of β-nitrostyrene, the reaction mixture was cooled to 8° C., and the precipitated product was filtered off, washed with water, and dried in air. The yield of product melting at 85° C.–87° C. (prior sintering) was 29.0 grams (93%).

Repeated recrystallizations without heating from methylene chloride-hexane and methylene chloride-methanol solutions gave pure α-(nitromethyl)benzyl 1-piperidinecarbodithioate melting at 86° C.–90.5° C. (prior sintering).

Analysis Calculated for $C_{14}H_{18}N_2S_2O_2$: C, 54.16; H, 5.84; N, 9.03; S, 20.66. Found: C, 54.35; H, 5.80; N, 8.87; S, 20.89.

EXAMPLE 17

2,4-Dichloro-α-(nitromethyl)benzyl Dimethyldithiocarbamate

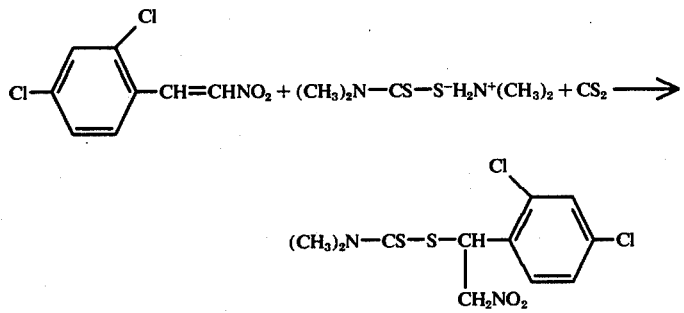

2,4-Dichloro-β-nitrostyrene (6.6 grams, 0.030 mole) was added to a stirred solution of dimethylammonium dimethyldithiocarbamate (5.1 grams, 0.030 mole) and carbon disulfide (1.8 ml., 0.030 mole) in methanol (30 ml.). The temperature of the resulting reaction was 16°–32° C. After 2 hours at room temperature, the precipitated product was filtered off, washed with cold methanol, and dried in air. Recrystallization without heating was accomplished by dissolving the sample in acetone and then adding absolute ethanol to give 2,4-dichloro-α-(nitromethyl)-benzyl dimethyldithiocarbamate melting at 127° C.–128° C.

Analysis Calculated for $C_{11}H_{12}N_2S_2O_2Cl_2$: C, 39.05; H, 3.27; N, 8.28; S, 18.95; Cl, 20.89. Found: C, 39.19; H, 3.53; N, 8.25; S, 18.92; Cl, 21.17.

EXAMPLE 18

α-(1-Nitroethyl)benzyl Dimethyldithiocarbamate

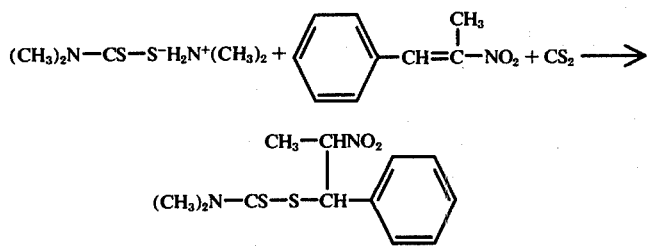

As in Example 17, reaction of (2-nitro-2-propenyl)-benzene with dimethylammonium dimethyldithiocarbamate in the presence of carbon disulfide, gave α-(1-nitroethyl)benzyl dimethyldithiocarbamate melting at 92° C.–94° C. when recrystallized without heating from acetone-ethanol solution.

Analysis Calculated for $C_{12}H_{16}N_2S_2O_2$: C, 50.67; H, 5.67; N, 9.85; S, 22.55. Found: C, 50.93; H, 5.71; N, 9.79; S, 22.80.

EXAMPLE 19

α-(Nitromethyl)benzyl Diethyldithiocarbamate

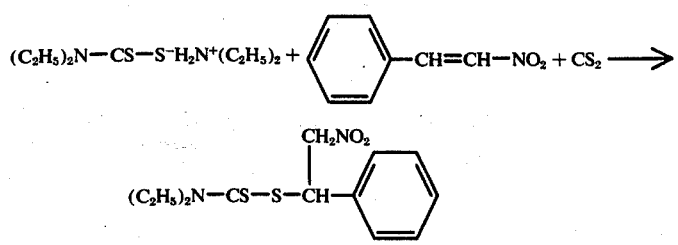

As in Example 17, reaction of β-nitrostyrene with diethylammonium diethyldithiocarbamate in the presence of carbon disulfide gave α-(nitromethyl)benzyl diethyldithiocarbamate melting at 81° C.–82.5° C. when recrystallized without heating from acetone-2-propanol solution.

Analysis Calculated for $C_{13}H_{18}N_2S_2O_2$: C, 52.32; H, 6.08; N, 9.39; S, 21.49. Found: C, 51.79; H, 6.04; N, 9.24; S, 21.03.

EXAMPLE 20

α,α'-Bis(nitromethyl)-p-phenylenedimethylene Dimethyldithiocarbamate

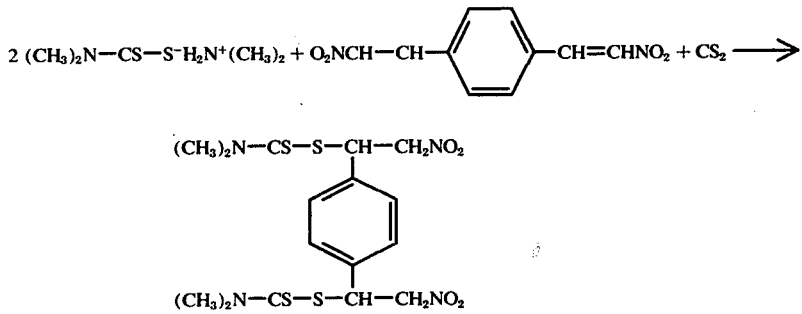

As in Example 17, reaction of one mole of 1,4-bis(2-nitrovinyl)benzene with two moles of dimethylammonium dimethyldithiocarbamate in the presence of carbon disulfide gave α,α'-bis(nitromethyl)-p-phenylenedimethylene dimethyldithiocarbamate, which did not have a definite melting point.

Analysis Calculated for $C_{16}H_{22}N_4S_4O_4$: C, 41.53; H, 4.79; N, 12.11; S, 27.72. Found: C, 41.64; H, 5.06; N, 12.10; S, 27.54.

EXAMPLE 21

2-Acetoxy-3-methoxy-α-(nitromethyl)benzyl Dimethyldithiocarbamate

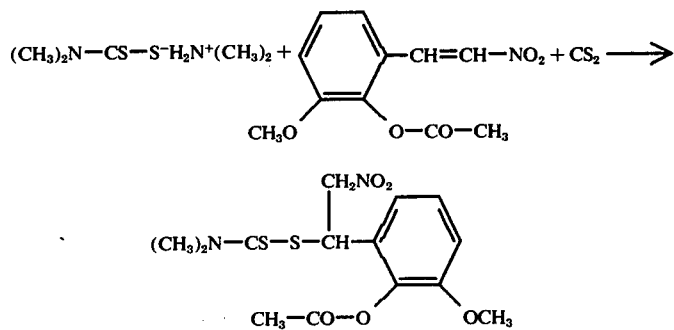

As in Example 17, reaction of 2-methoxy-6-(2-nitrovinyl)phenyl acetate from Example 22 with dimethylammonium dimethyldithiocarbamate in the presence of carbon disulfide gave 2-acetoxy-3-methoxy-α-(nitromethyl)benzyl dimethyldithiocarbamate melting at 124° C.–125.5° C. after recrystallization without heating from dimethylformamide-methanol solution.

Analysis Calculated for $C_{14}H_{18}N_2S_2O_5$: C, 46.91; H, 5.06; N, 7.82; S, 17.89. Found: C, 46.74; H, 5.19; N, 7.71; S, 17.89.

EXAMPLE 22

2-Methoxy-6-(2-nitrovinyl)phenyl Acetate

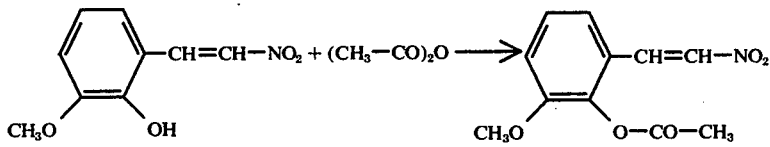

A mixture of 2-methoxy-6-(2-nitrovinyl)phenol (29.0 grams, 0.15 mole) and sodium acetate (12.4 grams, 0.15 mole) in acetic anhydride (100 ml.) was refluxed for 4 hours and then poured into ice water. The resulting semi-solid precipitate was dissolved in hot 95% ethanol. Cooling the solution precipitated the crude product which was purified for analysis by chromatography on silica gel with methylene chloride as elutant. The purified 2-methoxy-6-(2-nitrovinyl)phenyl acetate melted at 128° C.–129° C.

Analysis Calculated for $C_{11}H_{11}NO_5$: C, 55.70; H, 4.67; N, 5.90. Found: C, 55.88; H, 4.76; N, 5.81.

EXAMPLE 23

2-Chloro-5-nitro-α-(nitromethyl)benzyl Dimethyldithiocarbamate

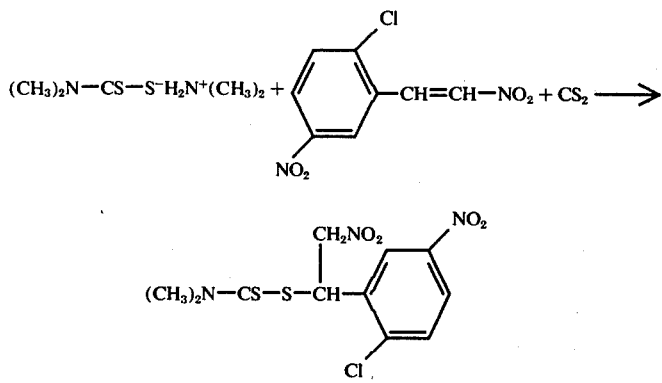

As in Example 17, reaction of 2-chloro-β,5-dinitrostyrene with dimethylammonium dimethyldithiocarbamate in the presence of carbon disulfide gave 2-chloro-5-nitro-α-(nitromethyl)-benzyl dimethyldithiocarbamate melting at 120° C.–121° C. after recrystallization without heating from acetone-methanol solution.

Analysis Calculated for $C_{11}H_{12}N_3S_2O_4Cl$: C, 37.77; H, 3.46; N, 12.01; S, 18.33; Cl, 10.13. Found: C, 37.81; H, 3.44; N, 12.01; S, 18.39; Cl, 10.11.

EXAMPLE 24

4-Acetoxy-α-(nitromethyl)benzyl Dimethyldithiocarbamate

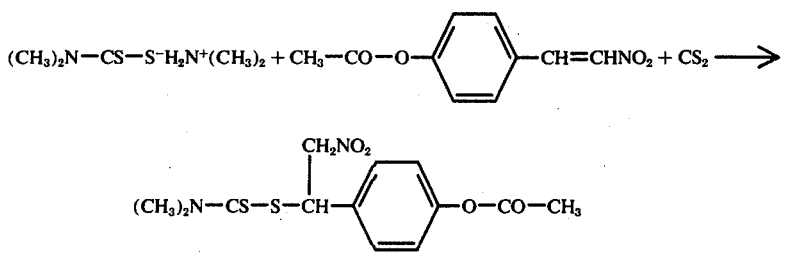

As in Example 17, reaction of 4-acetoxy-β-nitrostyrene with dimethylammonium dimethyldithiocarbamate in the presence of carbon disulfide gave 4-acetoxy-α-(nitromethyl)benzyl dimethyldithiocarbamate melting at 116° C.–118° C. after recrystallization without heating from acetone-methanol solution.

Analysis Calculated for $C_{13}H_{16}N_2S_2O_4$: C, 47.55; H, 4.91; N, 8.53; S, 19.53. Found: C, 47.52; H, 4.80; N, 8.35; S, 19.58.

EXAMPLE 25

3,4-Dimethoxy-α-(nitromethyl)benzyl Dimethyldithiocarbamate

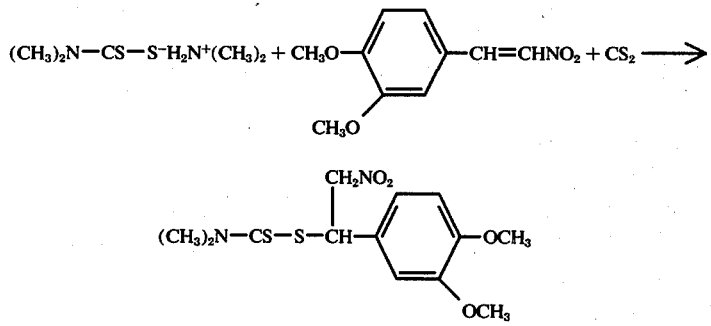

As in Example 17, reaction of 3,4-dimethoxy-β-nitrostyrene with dimethylammonium dimethyldithiocarbamate in the presence of carbon disulfide gave 3,4-dimethoxy-α-(nitromethyl)-benzyl dimethyldithiocarbamate melting at 108° C.–110° C. after recrystallization without heating from acetone-methanol solution.

Analysis Calculated for $C_{13}H_{18}N_2S_2O_4$: C, 47.26; H, 5.49; N, 8.48; S, 19.41. Found: C, 47.19; H, 5.50; N, 8.33; S, 19.34.

EXAMPLE 26 p-Isopropyl-α-(nitromethyl)benzyl Dimethyldithiocarbamate

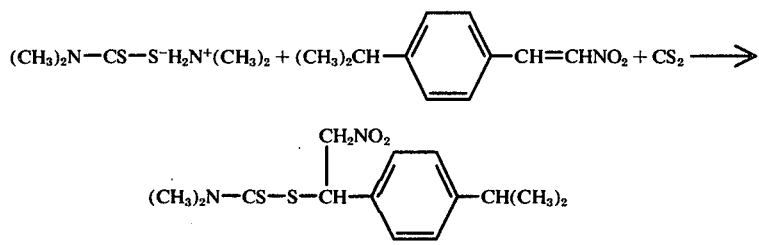

As in Example 17, reaction of p-isopropyl-β-nitrostyrene with dimethylammonium dimethyldithiocarbamate in the presence of carbon disulfide gave p-isopropyl-α-(nitromethyl)benzyl dimethyldithiocarbamate melting at 119° C.–120° C. after recrystallization without heating from acetone-methanol solution.

Analysis Calculated for $C_{14}H_{20}N_2S_2O_2$: C, 53.82; H, 6.45; N, 8.97; S, 20.52. Found: C, 53.74; H, 6.28; N, 8.99; S, 20.46.

EXAMPLE 27 o-Chloro-α-(nitromethyl)benzyl Dimethyldithiocarbamate

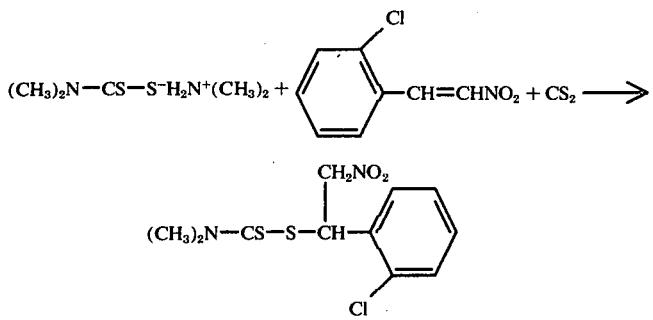

As in Example 17, reaction of o-chloro-β-nitrostyrene with dimethylammonium dimethyldithiocarbamate in the presence of carbon disulfide gave o-chloro-α-(nitromethyl)benzyl dimethyldithiocarbamate melting at 102° C.–103.5° C. when recrystallized without heating from acetone-methanol solution.

Analysis Calculated for $C_{11}H_{13}N_2S_2O_2Cl$: C, 43.34; H, 4.30; N, 9.19; S, 21.04. Found: C, 43.17; H, 4.02; N, 9.22; S, 21.14.

EXAMPLE 28

3,4-(Methylenedioxy)-α-(nitromethyl)benzyl Dimethyldithiocarbamate

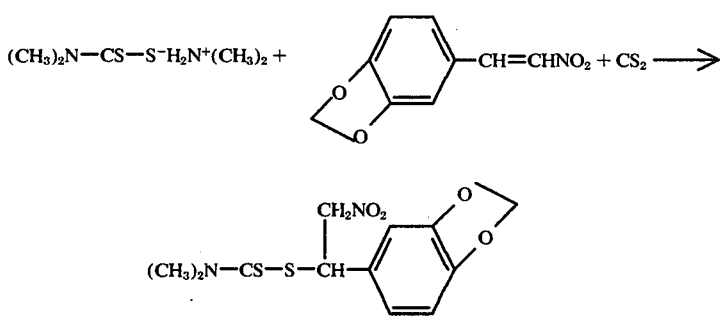

As in Example 17, reaction of 3,4-(methylenedioxy)-β-nitrostyrene with dimethylammonium dimethyldithiocarbamate in the presence of carbon disulfide gave 3,4-(methylenedioxy)-α-(nitromethyl)benzyl dimethyldithiocarbamate melting at 122° C.–124° C. when recrystallized without heating from acetone-ethanol solution.

Analysis Calculated for $C_{12}H_{14}N_2S_2O_4$: C, 45.85; H, 4.49; N, 8.91; S, 20.40. Found: C, 46.06; H, 4.53; N, 8.97; S, 20.51.

EXAMPLE 29 p-Methoxy-α-(nitromethyl)benzyl Dimethyldithiocarbamate

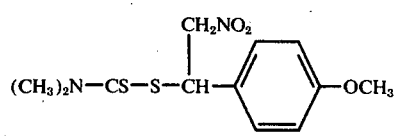

As in Example 17, reaction of p-methoxy-β-nitrostyrene with dimethylammonium dimethyldithiocarbamate in the presence of carbon disulfide gave p-methoxy-α-(nitromethyl)benzyl dimethyldithiocarbamate melting at 86° C.–89° C. when recrystallized without heating from acetone-methanol solution.

Analysis Calculated for $C_{12}H_{16}N_2S_2O_3$: C, 47.98; H, 5.37; N, 9.32; S, 21.35 Found: C, 48.19; H, 5.44; N, 9.25; S, 21.21.

EXAMPLE 30 p-Bromo-α-(nitromethyl)benzyl Dimethyldithiocarbamate

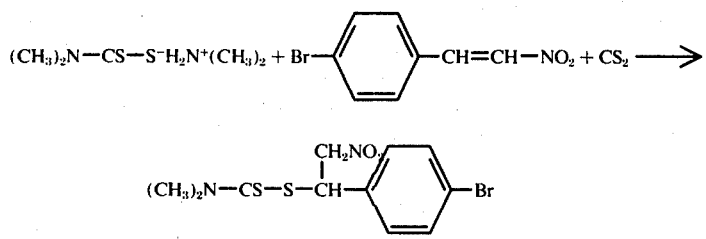

As in Example 17, reaction of p-bromo-β-nitrostyrene with dimethylammonium dimethyldithiocarbamate in the presence of carbon disulfide gave p-bromo-α-(nitromethyl)benzyl dimethyldithiocarbamate melting at 79° C.–81° C. when recrystallized without heating from acetone-ethanol solution.

Analysis Calculated for $C_{11}H_{13}N_2S_2O_2Br$: C, 37.82; H, 3.75; N, 8.02; S, 18.36; Br, 22.88. Found: C, 37.73; H, 3.80; N, 8.05; S, 18.21; Br, 22.93.

EXAMPLE 31

1-Naphthyl-2-nitroethyl Dimethyldithiocarbamate

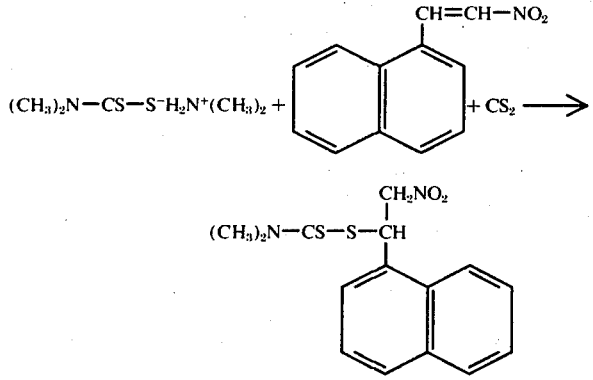

As in Example 17, reaction of 1-(2-nitrovinyl)naphthalene with dimethylammonium dimethyldithiocarbamate in the presence of carbon disulfide gave 1-naphthyl-2-nitroethyl dimethyldithiocarbamate melting at 136° C.–138° C. when recrystallized without heating from dimethylformamide-methanol solution.

Analysis Calculated for $C_{15}H_{16}N_2S_2O_2$: C, 56.23; H, 5.03; N, 8.74; S, 20.01. Found: C, 56.29; H, 5.05; N, 9.00; S, 20.15.

EXAMPLE 32

α-(Nitromethyl)furfuryl Dimethyldithiocarbamate

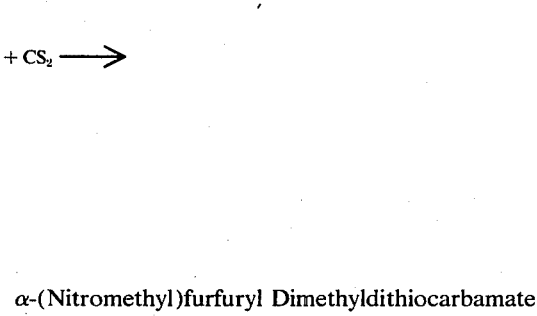

As in Example 17, reaction of 2-(2-nitrovinyl)furan with dimethylammonium dimethyldithiocarbamate in the presence of carbon disulfide gave α-(nitromethyl)furfuryl dimethyldithiocarbamate melting at 67° C.–68° C. after recrystallization from methanol.

Analysis Calculated for $C_9H_{12}N_2S_2O_3$: C, 41.52; H, 4.65; N, 10.76; S, 24.63. Found: C, 41.61; H, 4.54; N, 10.79; S, 24.71.

EXAMPLE 33

α-(Nitromethyl)-2-thenyl Dimethyldithiocarbamate

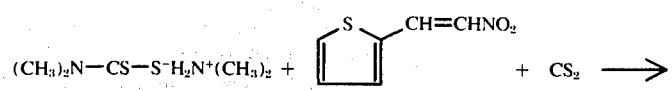

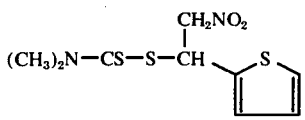

As in Example 17, reaction of 2-(2-nitrovinyl)thiophene with dimethylammonium dimethyldithiocarbamate in the presence of carbon disulfide gave α-(nitromethyl)-2-thenyl dimethyldithiocarbamate melting at 88° C.–90° C. when recrystallized without heating from acetone-ethanol solution.

Analysis Calculated for $C_9H_{12}N_2S_3O_2$: C, 39.10; H, 4.38; N, 10.13; S, 34.80. Found: C, 38.95; H, 4.36; N, 9.91; S, 34.98.

EXAMPLE 34

5-Chloro-α-(nitromethyl)-2-thenyl Dimethyldithiocarbamate

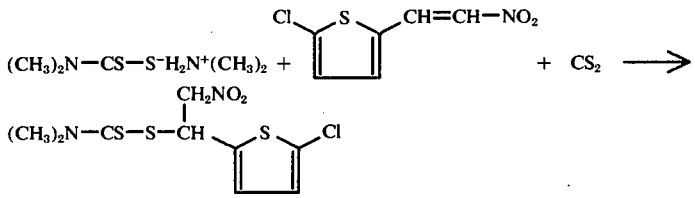

As in Example 17, reaction of 2-chloro-5-(2-nitrovinyl)thiophene with dimethylammonium dimethyldithiocarbamate in the presence of carbon disulfide gave 5-chloro-α-(nitromethyl)-2-thenyl dimethyldithiocarbamate melting at 76° C.–77° C., after recrystallization without heating from acetone-methanol solution.

Analysis Calculated for $C_9H_{11}N_2S_3O_2Cl$: C, 34.77; H, 3.57; N, 9.01; S, 30.95; Cl, 11.41. Found: C, 34.95; H, 3.62; N, 9.05; S, 30.99; Cl, 11.31.

EXAMPLE 35

α-(Nitromethyl)benzyl N-Methyldithiocarbanilate and a Related Compound

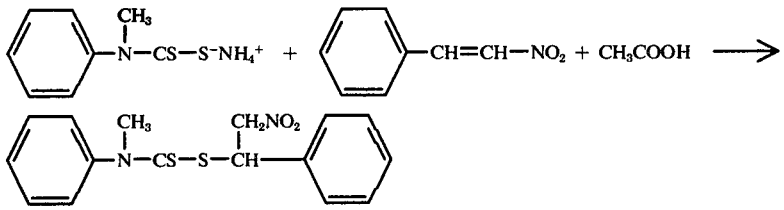

Ammonium N-methyldithiocarbanilate (15.0 grams, 0.075 mole) is added in four equal portions to a solution of β-nitrostyrene (11.2 grams, 0.075 mole) in 100 ml. of methanol. After each addition of ammonium N-methyldithiocarbanilate, acetic acid (1.1 grams, 0.019 mole) is added. The reaction temperature is maintained at 7° C.–10° C. during the additions, then the reaction mixture is allowed to warm to 31° C. and the crude yellow product, melting point 102° C.–110° C. (viscous melt), weight 12.5 grams, is filtered off. Recrystallizations without heat from methylene chloride-methanol give 5.0 grams of the off-white product, melting point 110.5° C.–114° C. For further purification, the product is recrystallized without heat from aqueous acetone, acetone and methylene chloride-methanol, consecutively, giving pure α-(nitromethyl)-benzyl N-methyldithiocarbanilate, melting point 111° C.–116° C., as shown by infrared and nuclear magnetic resonance spectra and elemental analysis.

Analysis Calculated for $C_{16}H_{16}N_2S_2O_2$: C, 57.81; H, 4.85; N, 8.43; S, 19.29. Found: C, 57.59; H, 4.83; N, 8.32; S, 19.69.

Reaction of 3,4-dimethoxy-β-nitrostyrene with ammonium ethyldithiocarbanilate by the above procedure yields 3,4-dimethoxy-α-(nitromethyl)benzyl ethyldithiocarbanilate.

EXAMPLE 36

α-(Nitromethyl)benzyl Dimethyldithiocarbamate

β-Nitrostyrene (14.9 grams, 0.10 mole) is added in portions to a stirred solution of dimethylammonium dimethyldithiocarbamate (8.3 grams, 0.05 mole) and carbon disulfide (3.8 grams, 0.05 mole). The temperature is maintained at 16° C.–26° C. during the addition; then the reaction mixture is cooled to 5° C. and the precipitate of α-(nitromethyl)benzyl dimethyldithiocarbamate is filtered off, washed with cold methanol and water, and dried in air. The yield of product, melting point 102° C.–108° C. (sinter 100° C.), is 25.3 grams (94%).

Similarly, gradual addition of dimethylamine (45.1 grams, 1 mole) to a methanol solution of carbon disulfide (83.6 grams, 1.1 mole) and β-nitrostyrene (149.1 grams, 1 mole) at 10° C.–30° C. yields α-(nitromethyl)-benzyl dimethyldithiocarbamate.

EXAMPLE 37

Spore Germination

The activity of the compounds of the invention for controlling pathogenic organisms reponsible for diseases in agricultural crops is further demonstrated by the following tests employing the organisms *Monillinia*

*frusticola*, the pathogen responsible for American brown rot in stone fruits; *Stemphylium sarcinaeforme*, the pathogen which incites leaf spot in legumes; and *Aspergillus niger*, the saprophyte responsible for degradation of textiles, fabrics, leather, and vegetables.

The test procedure involves the preparation of a 100, 10 or 1 ppm. suspension of test compound in water. The solutions are placed in one dram "opticlear" vials and separately inoculated with one drop of a spore suspension prepared from 7-day cultures of *Aspergillus niger* and 14-day old cultures of *Monilinia fructicola* and *Stemphylium sprcinaeforme*, all grown on potato-dextrose agar. The vials containing the separately inoculated solutions of test compounds are then capped and placed on a rotating tumbler for 24 hours to assure contact of the organism with the test compound. After 24 hours, the vials are removed and examined for inhibition of growth of mycelium.

The data obtained for the title compounds of the indicated examples are presented in Table I below.

TABLE I

| Compound of Example | % Inhibition of Spore Germination | | | | | | | | |
|---|---|---|---|---|---|---|---|---|---|
| | Monllinia Fructicola | | | Stemphyllum Sarciaanforme | | | Aspergillus Niger | | |
| | Concentration (ppm.) | | | | | | | | |
| | 100 | 10 | 1 | 100 | 10 | 1 | 100 | 10 | 1 |
| 1 | 100 | 100 | 100 | 100 | 100 | 100 | 100 | 100 | 100 |
| 7 | 100 | 100 | 0 | 0 | | | 100 | 100 | 0 |
| 13 | 100 | 100 | 100 | 100 | 100 | 100 | 100 | 100 | 100 |
| 30 | 100 | 100 | 100 | 100 | 100 | 0 | 100 | 100 | 0 |
| 29 | 100 | 100 | 0 | 100 | 100 | 0 | 100 | 0 | 0 |
| 28 | 100 | 100 | 100 | 100 | 0 | 0 | 100 | 100 | 100 |
| 33 | 100 | 100 | 100 | 100 | 100 | 100 | 100 | 100 | 0 |
| 27 | 100 | 100 | 0 | 100 | 100 | 100 | 100 | 100 | 0 |
| 25 | 100 | 100 | 0 | 100 | 100 | 100 | 100 | 100 | 0 |
| 9 | 100 | 0 | 0 | 100 | 0 | 0 | 100 | 0 | 0 |
| 6 | 100 | 100 | 100 | 100 | 100 | 100 | 100 | 100 | 0 |
| 31 | 100 | 0 | 0 | 100 | 0 | 0 | 100 | 0 | 0 |
| 24 | 100 | 100 | 0 | 0 | | | 100 | 100 | 0 |
| 34 | 100 | 100 | 0 | 100 | 100 | 0 | 100 | 100 | 0 |
| 10 | 100 | 100 | 100 | 100 | 100 | 100 | 100 | 100 | 100 |

TABLE II

| Compound of Example | Antibacterial Activity | | |
|---|---|---|---|
| | Aerobacter aerogenes | Staphylococcus aureus | Xanthomonas vesicatoria |
| | Concentration (ppm.) | | |
| | 100 | 100 | 100 |
| 1 | 0 | 5 | 0 |
| 7 | 9 | 9 | 5 |
| 13 | 5 | 5 | 5 |
| 8 | 0 | 5 | 0 |
| 17 | 0 | 5 | 0 |
| 30 | 0 | 5 | 0 |
| 28 | 9 | 5 | 5 |
| 33 | 0 | 5 | 0 |
| 18 | 0 | 5 | 0 |
| 27 | 9 | 5 | 5 |
| 26 | 0 | 5 | 0 |
| 25 | 5 | 5 | 5 |
| 9 | 0 | 5 | 0 |
| 6 | 9 | 9 | 9 |
| 10 | 9 | 9 | 5 |
| 11 | 0 | 5 | 0 |

EXAMPLE 38

Antibacterial Activity

Test compounds are added to separate test tubes of deionized sterile water at the rate of 100 ppm. final concentration. Separate treated tubes are inoculated with one drop of 24-hour broth cultures of *Aerobacter aerogenes, Staphylococcus aureus*. or *Xanthomonas vesicatoria*. The tubes are incubated for 24 hours at room temperature. At the end of 24 hours, 1.1 ml. of sterile peptone broth is added to tubes aseptically, and the tubes are incubated at 37° C. for 24 hours. At the end of 24 hours, all tubes are clear so subcultures are made to new untreated tubes and these incubated for 72 hours at 37° C. At the end of this period, all tubes are examined and rated.

0 = No Effect
9 = Kill of Bacteria
5 = Stasis, but not Kill of all Bacteria

The data obtained for the title compounds of the indicated examples are presented in Table II below.

EXAMPLE 39

Test compounds were incorporated in a Sabouraud's dextrose agar in an amount sufficient to provide the active ingredient in a concentration of about 100 ppm. A 20-ml. sample of the agar mixture is placed in a petri dish and permitted to solidify. An agar sample is inoculated with the test organism set forth below and then covered and incubated for a period of about 72 hours at 23° C. After incubation, growth observations are made. The test results are recorded and the test is repeated twice for the purpose of comparision.

The data obtained with a variety of test organisms is shown in the table below, and ratings are shown as 0 or 5. 0 indicates no control, 5 indicates 100% effectiveness of the test compound against the specified organism.

Abbreviations are as follows:
An = *Aspergillus niger*
Fl = *Fusarium lycopersici*
Mf = *Monilinia fructicola*
Pd = *Pythium de Baryanum*
Rs = *Rhizoctonia solani*
Ss = *Stemphylium sarcinaeforme*
Ps = *Pseudomonas solaracaerum*
Cl = *Collectotrichum lagenarium*
Va = *Verticillium albo-atrum*

The data obtained for the title compounds of the indicated examples are presented in Table III below.

TABLE III

| Compound of Example | 100 ppm. Agar Dilution Plate | | | | | | | | |
|---|---|---|---|---|---|---|---|---|---|
| | An | Fl | Mf | Pd | Ra | Ss | Ps | Cl | Va |
| 1  | 0 | 0 | 5 | 0 | 0 | 5 | C | 5 | 0 |
| 2  | 0 | 0 | 0 | 0 | 0 | 0 | 0 | 5 | 0 |
| 7  | 0 | 0 | 5 | 0 | 5 | 5 | 0 | 5 | 5 |
| 13 | 0 | 5 | 5 | 5 | 0 | 5 | 0 | 5 | 5 |
| 8  | 0 | 0 | 5 | 0 | 0 | 0 | 0 | 0 | 5 |
| 17 | 0 | 0 | 0 | 0 | 0 | 0 | 0 | 5 | 5 |
| 30 | 0 | 0 | 5 | 5 | 5 | 0 | 0 | 5 | 0 |
| 28 | 0 | 0 | 5 | 5 | 0 | 5 | 0 | 5 | 5 |
| 33 | 0 | 0 | 5 | 0 | 0 | 5 | 0 | 5 | 0 |
| 18 | 0 | 5 | 5 | 5 | 5 | 5 | 0 | 5 | 5 |
| 19 | 0 | 0 | 5 | 0 | 0 | 0 | 0 | 0 | 0 |
| 27 | 0 | 5 | 5 | 5 | 0 | 5 | 0 | 5 | 5 |
| 26 | 0 | 0 | 5 | 5 | 5 | 5 | 0 | 5 | 5 |
| 25 | 0 | 0 | 5 | 5 | 0 | 5 | 0 | 5 | 5 |
| 9  | 0 | 0 | 0 | 0 | 0 | 0 | 0 | 5 | 0 |
| 6  | 5 | 5 | 5 | 5 | 5 | 5 | 0 | 5 | 5 |
| 31 | 0 | 0 | 5 | 5 | 5 | 5 | 0 | 5 | 5 |
| 24 | 0 | 0 | 5 | 0 | 0 | 5 | 0 | 5 | 5 |
| 34 | 0 | 0 | 0 | 0 | 5 | 0 | 0 | 5 | 0 |
| 10 | 5 | 5 | 5 | 5 | 5 | 5 | 0 | 5 | 5 |
| 11 | 0 | 0 | 5 | 0 | 0 | 0 | 0 | 5 | 0 |

EXAMPLE 40

Apple Scab (*Venturia inaequalis*) on Field-Grown Trees

The compound of Example 13 was applied as a foliar spray for ten applications at weekly intervals from May 1 through July 2, and then two more sprays on a 2-week schedule ending on July 31.

The active compound was applied as a 50% wettable powder having the following compositions:

50% Active Compound (Example 13)
1% Aerosol OS
2% Cellosize QP 15000
4% Blancol N
43% Kaolinite 41

Rates of 50% wettable applied were:

2 pounds/100 gallons of water
1 pound/100 gallons of water
Three tree replicates of each rate
Variety: Red Delicious were used.

Trees at the 2-pound rate remained free of scab all season long. The 1-pound rate showed a trace of scab at the end of the season. No phytotoxicity was observed.

Example 41

Field-Grown Tomatoes and Cantaloupes

All compounds were applied at 4.8 pounds/100 gallons and 2.4 pounds/100 gallons of water per acre.

The tomato varieties used were Rutgers and Manalucie. These were treated eight times at weekly intervals. No phytotoxicity was noted with dry compound at any rate. Too little disease developed to rate for disease control.

The same compounds and rates were applied to cantaloupe for five weekly sprays. No phytotoxicity with dry compound, and too little disease to rate for disease control.

Formulations used were prepared as follows:

50% Wettable Powder - Compound Example 1
    50% Test Compound (Example 1)
    1.1% Aerosol OS
    3.5% Marasperse CB
    45.4% Kaolinite 41
50% Wettable Powder - Test Compound Example 18
    50% Test Compound (Example 18)
    10% Aerosol OS
    3.5% Marasperse CB
    45.5% Kaolinite 41
50% Wettable Powder - Test Compound Example 13
    50% Test Compound (Example 13)
    1% Aerosol OS
    2% Cellosize CP 15000
    4% Blancol N
    43% Kaolinite 41

EXAMPLE 42

Solutions of various concentrations of test compounds are prepared in a mixture of equal parts by weight of acetone and water. The foliage of Bonny Best tomato plants with four true leaves. Early Marketeer cucumber plants with two true leaves, Nato variety rice plants and Red Delicious apple seedlings with eight of 14 true leaves were sprayed to run-off with the test solutions. The plants were allowed to dry and were then sprayed with a mixed inoculum of the cucumber anthracnose (*Colletotrichum lagenarium*), tomato late blight (*Phytophthora infestans*), rice blast (*Piricularia oryzae*), and apple scab (*Venturia inaequalis*). The sprayed plants were held for 5 days in an incubation room under a water-saturated atmosphere at 18° C., after which time the plants were removed and lesion counts were made. The results obtained, expressed in terms of the disease control index for the title compounds of the indicated examples are presented in the tables below.

TABLE IV

| Compound Example Number | Cucumber Anthracnose (Colletotrichum lagenarium) | |
|---|---|---|
| | Dosage in ppm. | |
| | 500 | 1000 |
| 7  | 2 | 2 |
| 13 | 5 | 5 |
| 8  | 5 | 5 |
| 28 | 5 | 5 |
| 18 | 5 | 5 |
| 15 | 5 | N.T. |
| 3  | 4 | N.T. |
| 16 | 5 | N.T. |

Abbreviations
5 = clean, no disease
4 = trace of disease
3 = slight disease
2 = moderate disease
1 = severe disease
0 = like controls
N.T. = no test

TABLE V

| Compound Example Number | Tomato Late Blight (Phytophthora infestans) | | | |
|---|---|---|---|---|
| | Dosage in ppm. | | | |
| | 1200 | 600 | 300 | 150 |
| 1  | 5 | 4 | 4 | 3 |
| 2  | 5 | 5 | 4 | 4 |
| 13 | 5 | 5 | 5 | 5 |
| 8  | N.T. | N.T. | 5 at 500 | 5 at 100 |
| 17 | 5 | 5 | 4 | 0 |
| 30 | 4 | 3 | 3 | 2 |
| 29 | 5 | 5 | 5 | 5 |
| 28 | N.T. | N.T. | 5 at 500 | 5 at 100 |

TABLE V-continued

| Compound Example Number | Tomato Late Blight (Phytophthora infestans) Dosage in ppm. | | | |
|---|---|---|---|---|
| | 1200 | 600 | 300 | 150 |
| 20 | 5 | 4 | 3 | 3 |
| 33 | N.T. | N.T. | 5 | 5 |
| 18 | N.T. | N.T. | 5 at 500 | 5 at 100 |
| 32 | 5 | 5 | 4 | 4 |
| 19 | 3 | 3 | 3 | 3 |
| 27 | 4 | 4 | 2 | 2 |
| 26 | 5 | 4 | 4 | 3 |
| 25 | 5 | 5 | 5 | 5 |
| 31 | N.T. | N.T. | 5 at 500 | 5 at 100 |
| 24 | N.T. | N.T. | 5 at 500 | 3 at 100 |
| 34 | N.T. | N.T. | 3 at 500 | N.T. |
| 23 | N.T. | N.T. | 5 at 500 | 5 at 100 |
| 21 | N.T. | N.T. | 5 at 500 | N.T. |
| 10 | N.T. | N.T. | 5 at 500 | 4 at 100 |
| 11 | N.T. | N.T. | 4 at 500 | 3 at 100 |
| 12 | N.T. | N.T. | 5 | 5 |
| 3 | N.T. | N.T. | 4 | 4 |

TABLE VI

| Compound Example Number | Rice Blast (Piricularia Oryzae) Dosage in ppm. | | | |
|---|---|---|---|---|
| | 1200 | 600 | 300 | 150 |
| 1 | 3 | 3 | 2 | 2 |
| 2 | 5 | 5 | 4 | 4 |
| 7 | 5 | 4 | 2 | 2 |
| 13 | 5 | 5 | 5 | 5 |
| 8 | N.T. | N.T. | 5 at 500 | 5 at 100 |
| 17 | 5 | 5 | 5 | 3 |
| 30 | 5 | 5 | 5 | 5 |
| 29 | 5 | 5 | 5 | 4 |
| 28 | 5 | 5 | 0 | 0 |
| 33 | N.T. | N.T. | 5 | 5 |
| 18 | N.T. | N.T. | 5 at 500 | 5 at 100 |
| 32 | 5 | 5 | 0 | 0 |
| 19 | 5 | 5 | 3 | 3 |
| 27 | 4 | 4 | 4 | 2 |
| 26 | 5 | 5 | 4 | 4 |
| 25 | 4 | 5 | 4 | 3 |
| 9 | 4 | 3 | 2 | 0 |
| 31 | N.T. | N.T. | 5 at 500 | 4 at 75 |
| 24 | N.T. | N.T. | 4 at 500 | 3 at 75 |
| 34 | N.T. | N.T. | 3 at 500 | 1 at 75 |
| 23 | N.T. | N.T. | 4 at 500 | 3 at 75 |
| 21 | N.T. | N.T. | 4 at 500 | 3 at 75 |
| 10 | N.T. | N.T. | 5 at 500 | 4 at 75 |
| 11 | N.T. | N.T. | 4 at 500 | 3 at 75 |
| 12 | N.T. | N.T. | 5 | N.T. |
| 15 | N.T. | N.T. | 4 | 4 |
| 3 | N.T. | N.T. | 5 | 5 |
| 16 | N.T. | N.T. | 5 | 5 |

TABLE VII

| Compound Example Number | Apple Scab (Venturia inaequalis) Dosage in ppm. | | | |
|---|---|---|---|---|
| | 1200 | 600 | 300 | 150 |
| 1 | 3 | 3 | 3 | 0 |
| 2 | 5 | 5 | 5 | 5 |
| 7 | 5 | 0 | 0 | 0 |
| 13 | 5 | 5 | 5 | 5 |
| 8 | 5 | 5 | 5 | 4 |
| 17 | 5 | 5 | 5 | 0 |
| 30 | 5 | 5 | 5 | 5 |
| 29 | 5 | 5 | 5 | 5 |
| 28 | 5 | 5 | 0 | 0 |
| 33 | 5 | 5 | 5 | 5 |
| 18 | N.T. | N.T. | 5 at 500 | 5 at 100 |
| 32 | 5 | 5 | 0 | 0 |
| 19 | 5 | 5 | 0 | 0 |
| 27 | 5 | 0 | 0 | 0 |
| 26 | 5 | 0 | 0 | 0 |
| 25 | 5 | 5 | 5 | 5 |
| 31 | N.T. | N.T. | 4 at 500 | N.T. |
| 24 | N.T. | N.T. | 5 at 500 | N.T. |
| 23 | N.T. | N.T. | 4 at 500 | N.T. |
| 21 | N.T. | N.T. | 4 at 500 | N.T. |
| 11 | N.T. | N.T. | 5 at 500 | N.T. |

TABLE VII-continued

| Compound Example Number | Apple Scab (Venturia inaequalis) Dosage in ppm. | | | |
|---|---|---|---|---|
| | 1200 | 600 | 300 | 150 |
| 12 | N.T. | N.T. | 5 | 5 |
| 16 | N.T. | N.T. | 5 | 5 |

We claim:

1. A compound having the structure:

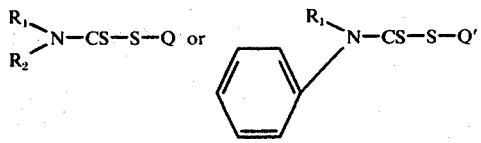

wherein Q represents

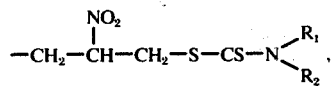

or

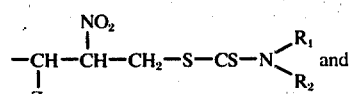

wherein Q' represents

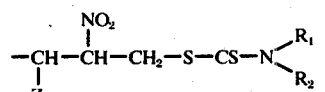

and where $R_1$ and $R_2$ are each loweralkyl $C_1$–$C_4$, or when $R_1$ and $R_2$ are taken together with N represent a piperidine or pyrrolidine nucleus; and Z is phenyl,

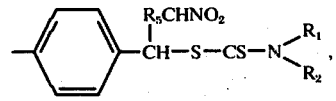

1-naphthyl, 2-furyl, 2-thienyl, 5-chloro-2-thienyl or substituted phenyl and $R_5$ is hydrogen or lower alkyl $C_1$–$C_4$.

2. A compound according to claim 1 having the formula:

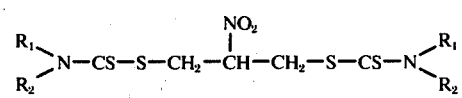

where $R_1$ and $R_2$ are each loweralkyl $C_1$–$C_4$, or when $R_1$ and $R_2$ are taken together with N form piperidine or pyrrolidine.

3. A compound according to claim 2:

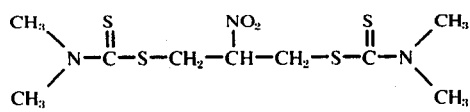

4. A compound according to claim 2:

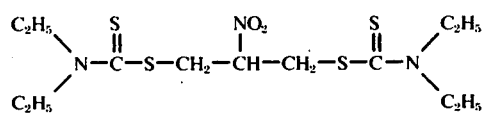

5. A compound according to claim 2:

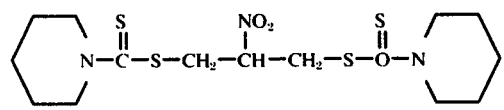

6. A process for the preparation of compounds according to claim 1 of the formula:

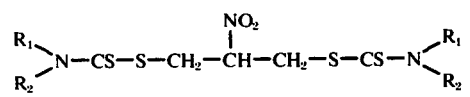

where $R_1$ and $R_2$ each represent loweralkyl $C_1$–$C_4$; comprising reacting about two mole equivalents of a dialkylammonium dialkyldithiocarbamate of the formula:

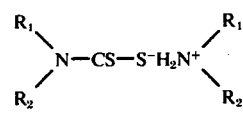

with about two mole equivalents of formaldehyde, and one mole equivalent of nitromethane in the presence of an aqueous lower alcohol and aqueous dimethylformamide solution containing about one mole equivalent of carbon disulfide, said reaction being carried out at a temperature between about 20° C. and 50° C.

7. A process for the preparation of compounds according to claim 1 of the formula:

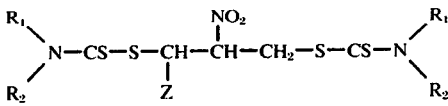

and

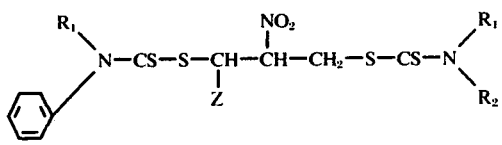

comprising reacting approximately equimolar amounts of a compound of the formula:

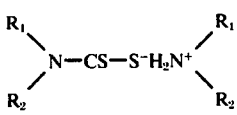

with about equimolar amounts of formaldehyde, carbon disulfide and a compound of the formula:

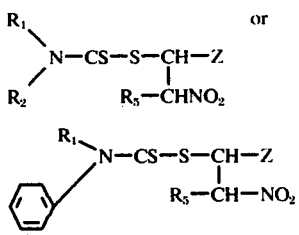

wherein $R_1$ and $R_2$ are each loweralkyl $C_1$–$C_4$ or when taken together with N form a piperidine or pyrrolidine nucleus; $R_5$ is hydrogen or loweralkyl $C_1$–$C_4$; and Z is a member of the group consisting of phenyl,

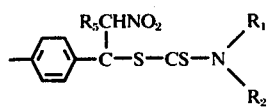

1-naphthyl, 1-furyl, 2-thienyl, 5-chloro-2-thienyl or substituted phenyl; in the presence of an aqueous lower alcohol or aqueous dimethylformamide mixture and at a temperature between about 20° C. and 50° C.

* * * * *